United States Patent [19]
Von Genk et al.

[11] 3,932,543
[45] Jan. 13, 1976

[54] PROCESS FOR HALOGENATION OF CONJUGATED DIENES TO DIHALOGENATED BUTENE PRODUCTS

[75] Inventors: Richard A. Von Genk; Carlos G. Cardenas, both of Jacksonville, Fla.

[73] Assignee: SCM Corporation, New York, N.Y.

[22] Filed: Apr. 13, 1973

[21] Appl. No.: 350,755

[52] U.S. Cl. .......................................... 260/654 H
[51] Int. Cl.² ........................................ C07C 21/04
[58] Field of Search ...................... 260/654 H, 660

[56] References Cited
UNITED STATES PATENTS

| | | | |
|---|---|---|---|
| 2,350,373 | 6/1944 | Soday | 260/654 H |
| 2,374,711 | 5/1945 | Soday | 260/654 H |
| 2,446,475 | 8/1948 | Hearne et al. | 260/654 R |
| 3,338,982 | 8/1967 | Leach et al. | 260/660 |
| 3,793,380 | 2/1974 | d'Ostrowick et al. | 260/648 C |

FOREIGN PATENTS OR APPLICATIONS

| | | | |
|---|---|---|---|
| 723,185 | 12/1965 | Canada | 260/654 R |

*Primary Examiner*—Delbert E. Gantz
*Assistant Examiner*—Joseph A. Boska
*Attorney, Agent, or Firm*—Richard H. Thomas

[57] ABSTRACT

In the process for halogenation of conjugated dienes with elemental halogen under halogenation conditions, the improvement for obtaining increased yield of dihalogenated butene products comprising forming the reaction mixture with a dipolar aprotic solvent vehicle resistant to halogenation under such conditions in the proportion of about 0.05–10 moles per mole of said diene. The invention has particular application in the chlorination of isoprene to 1,4-dichloro-2-methyl-2-butene and 1,2-dichloro-2-methyl-3-butene.

9 Claims, No Drawings

PROCESS FOR HALOGENATION OF CONJUGATED DIENES TO DIHALOGENATED BUTENE PRODUCTS

The present invention relates to the halogenation of conjugated dienes and particularly to obtaining an improved yield of dihalogenated butene products. The invention is particularly applicable to the chlorination of isoprene towards obtaining improved yields of 1,4-dichloro-2-methyl-2-butene and 1,2-dichloro-2-methyl-3-butene.

BACKGROUND OF THE INVENTION

The chlorination of isoprene under normal conditions is less than straightforward and results in the formation of a variety of products. In a simple addition reaction involving loss of one double bond, dichlorides are formed such as 1,4-dichloro-2-methyl-2-butene and 1,2-dichloro-2-methyl-3-butene. A competing reaction, however, is one of substitution rather than addition in which a hydrogen ion is given up resulting in the formation of monochlorides such as 2-chloromethyl-1,3-butadiene and 1-chloro-2-methyl-1,3-butadiene. The substitution reaction produces HCl as a by-product which in turn reacts with unreacted isoprene in an HCl addition reaction to give hydrochlorides or monochlorobutenes such as 1-chloro-3-methyl-2-butene and 2-chloro-2-methyl-3-butene. In the preparation of the dichloride addition products, the formation of these monochloride substitution and HCl addition products constitutes an undesirable loss. Chlorination under conditions reported in the literature was found to result in discouragingly low weight yields of the 1,4- and 1,2-dichlorides, e.g., less than 50–60%, based on the weight of isoprene consumed. On a theory yield basis, which is moles of dichloride product per mole of isoprene consumed, this amounts to a yield of less than about 25–30%.

SUMMARY OF THE INVENTION

In accordance with the present invention, it was found that improved yields of 1,2- and 1,4-dihalogenated butene products could be obtained by forming a reaction mixture of the conjugated dienes with a dipolar aprotic solvent vehicle which was resistant to the halogenation. Preferably the dipolar aprotic solvent is employed in the proportion of about 0.05–10 moles per mole of diene. A preferred solvent is dimethylformamide (DMF) with which optimum 1,4- and 1,2-dihalide weight yields of 140% or better, based on the weight of isoprene consumed, are obtained. Other suitable solvents are N,N-dimethylacetamide (DMA), hexamethylphosphoramide (HMPA), acetamide, N-methylpyrrolidone, dimethylsulfoxide (DMSO) and thioamides where the oxygen atom of the aforementioned solvents is replaced by sulfur. Also a mixture of solvents may be employed, and the solvent system can include limited amounts of water, in varying proportions. The reaction may be carried out at room temperature and preferably is carried out in the dark. Temperatures below ambient appear to offer no advantage. Preferred halogens are chlorine and bromine.

Optimization of the process is achieved by conversion or consumption of less than the 100% of the isoprene. Desirably the reaction is carried out to 50–80% conversion, the weight yield per mole of isoprene consumed declining slightly with increased conversion beyond 50%, i.e., use of chlorine in a mole ratio, per mole of isoprene, of more than 1:2. Higher conversions up to 100%, however, can be tolerated without the losses becoming undue.

In an embodiment of the invention, the 1,2 addition product formed in the halogenation reaction may be isomerized in the presence of diethylene glycol with a catalyst such as CuCl or $CuCl_2$, or by other known methods to increase the yield of the 1,4-dichloride addition product. The literature in this regard is replete with references to methods for the isomerization of dichlorobutadienes which methods largely can be applied to the isomerization of 1,2-dichloro-2-methyl-2-butene and other 1,2-dihalobutenes.

An excess of aprotic solvent is not necessary, satisfactory yields being achieved with, by way of example, isoprene/DMF mole ratios of about 6:1 (about 0.16 moles of solvent per mole of diene). As a general rule, economics dictate that the least amount of solvent possible, without sacrificing yield, should be employed. However, ratios of below about 0.05 moles solvent per mole of diene may provide weight yields of dichloride addition products which are less than satisfactory. Increases in solvent/isoprene mole ratios above about 1:6 do not tend to give proportionate increases in yield. A preferred range for the dipolar aprotic solvent is about 0.1–0.6 moles per mole of diene.

The following examples illustrate the present invention:

EXAMPLE 1

In the process in accordance with the present invention, isoprene (204 grams, 3.0 moles) was stirred in a 500 ml. 3-neck round bottom flask at 25±2°C. in the dark in the presence of 36.5 grams (0.5 moles) of N,N-dimethylformamide (DMF). Chlorine (215 grams, 3.0 moles) was added via a fritted tube over a period of 145 minutes. Samples were taken during the course of the addition, were washed with water and were analyzed by gas chromatography giving the following ratios of primary products:

TABLE 1

| Time | Moles $Cl_2$ Added Per Mole of Isoprene | Percent Substitution Products | Percent HCl Addition Products | Percent Desired Dichlorides | Percent Higher Mol. Wt. Cmpds. |
|---|---|---|---|---|---|
| 40 min. | .28 | 10.9 | — | 67.7 | — |
| 75 min. | .52 | 9.3 | — | 77.4 | — |
| 110 min. | .76 | 9.5 | 0.9 | 74.1 | 2.1 |
| 145 min. | 1.00 | 10.3 | 1.1 | 70.6 | 6.6 |

The weight yield of desired dichlorides, which were 1,2-dichloro-2-methyl-3-butene and cis- and trans-1,4-dichloro-2-methyl-2-butene, based on the weight of isoprene consumed, calculated to be about 144.5% after completion of addition. The primary substitution and HCl addition products were, respectively, 2-chloromethyl-1,3-butadiene, and 1-chloro-3-methyl-2-butene and 2-chloro-2-methyl-3-butene. It can be seen from Table 1 that the percentage of desired dichlorides decreased slightly after 75 minutes reaction time, or about 0.52 moles addition of chlorine per mole of isoprene. Experience indicates that weight yields of even higher than 144.5%, with the same reaction conditions, can be obtained by interrupting the addition of chlorine at about 0.50 moles. The ratio of 1,4-dichloride to 1,2-dichloride product was about 3:1 (74.6:25.4).

By comparison, the following results were obtained when no solvent was employed. Isoprene (204 grams, 3.0 moles) was stirred in a 500 ml. 3-neck round bottom flask at 0°C. in the dark, while 213 grams of chlorine (3.0 moles) was added via a fritted tube over a period of 195 minutes. Samples were taken during the course of the addition, were washed with water and analyzed. Gas chromatographic analysis of the product indicated the presence primarily of the substitution product (2-chloromethyl-1,3-butadiene) and the HCl addition products (1-chloro-3-methyl-2-butene and 2-chloro-2-methyl-3-butene), and of relatively low percentages of the desired dichlorides.

TABLE 2

| Time | Moles Cl₂ Added Per Mole of Isoprene | Percent Substitution Products | Percent HCl Addition Products | Percent Desired Dichlorides | Percent Higher Mol. Wt. Cmpds. |
|---|---|---|---|---|---|
| 37 min. | .27 | 24.2 | 30.2 | 31.8 | 1.7 |
| 70 min. | .50 | 22.8 | 34.5 | 29.3 | 1.6 |
| 105 min. | .73 | 20.4 | 29.4 | 29.4 | 2.7 |
| 195 min. | 1.00 | 5.2 | 22.6 | 26.8 | 21.7 |

The weight yield of desired dichlorides based on the amount of isoprene consumed calculated to be about 54.3% after completion of addition, as compared to the yield of about 144.8% of Table 1.

Although applicant is to be held to no particular theory as to the reason for the effectiveness of the chlorination reaction in accordance with the concepts of the present invention, it is surmised that the aprotic solvent serves a dual function, suppressing the substitution reaction and also consuming HCl formed thus decreasing the amounts of HCl addition products.

The following example illustrates the present invention with other solvents and conditions:

EXAMPLE 2

The following table gives yields for different solvents at different conditions, using isoprene as the starting material. The percentage yields are amounts of 1,2- and 1,4-dichloride product per weight of isoprene consumed. In each instance, the procedure of Example 1 was followed, the reaction being carried out in the dark. The data of Example 1 is also summarized in the following table for comparison.

TABLE 3

| Run | Temp. °C. | Moles Cl₂ per Mole 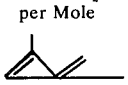 | Solvent | Moles Solvent Per Mole 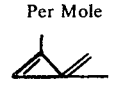 | Wt. Yield of 1,2- and 1,4-Dichlorides |
|---|---|---|---|---|---|
| Example 1 with solvent | 25° | 1.0 | DMF | 0.16 | 144% |
| Example 1 without solvent | 0° | 1.0 | — | — | 54% |
| 1. | 0° | 0.5 | DMA | 0.3 | 139% |
| 2. | 0° | 1.0 | DMA | 0.3 | 125% |
| 3. | 0° | 0.5 | DMF | 0.3 | 138% |
| 4. | 0° | 1.0 | DMF | 0.3 | 128% |
| 5. | 0° | 1.0 | DMF | 4.0 | 137% |
| 6. | 0° | 0.5 | HMPA | 0.3 | 145% |
| 7. | 25° | 0.5 | DMF | 0.3 | 144% |
| 8. | 25° | 0.5 | DMF | 0.6 | 136% |

All of the above runs, except that of Example 1 without solvent, are within the concepts of the present invention.

EXAMPLE 3

This example illustrates isomerization of the 1,2-dichloride to the 1,4-isomer. The isomerization is carried out with a catalyst such as CuCl or CuCl₂ preferably in the presence of a solvent. Improved yields were obtained with increased reaction time and temperature as shown in the following table:

TABLE 4

| Grams of 1,2-dichloride | Grams of Catalyst | Solvent | Conversion, % | | | | |
| | | | 1 hr. 25° | 1 hr. 40° | 2 hr. 40° | 1 hr. 70° | 2 hr. 70° |
|---|---|---|---|---|---|---|---|
| 2.5 | 0.2 CuCl₂ | 20 ml Diethylene Glycol | 11 9 | 10 | 11 | 59 | 94 |
| 2.5 | 0.2 CuCl | " | 20 | 67 | 90 | 96 | 95 |

In place of isoprene, the reactions of Example 1 may be successfully carried out with butadiene and other diolefins having a conjugated system of double bonds. Examples of other olefinic materials which can be halogenated are piperylene, cyclopentadiene, myrcene, ocimene, and α-terpinene. The resulting halogenated materials may be useful monomers or may be converted to the useful products or the intermediates of useful products, such as pharmaceuticals, flavor and perfume chemicals and pesticides, and also may have useful flame-retardant and biological properties.

Prior application Ser. No. 246,939, filed Apr. 24, 1972, by William Oroshnik now abandoned, assigned to assignee of the present application, describes a new process for making Vitamin A, carotenoid by-products of Vitamin A, and isomers thereof. One of the intermediates employed in the method of the application is isoprene chloroacetate (4-chloro-3-methylbut-2-enyl-acetate) which has the structure

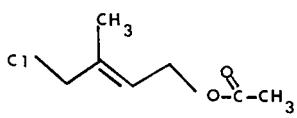

This compound may also be named 1-chloro-4-acetoxy-2-methyl-2-butene or 4-chloro-3-methyl-2-butene-1-yl acetate. The preparation of the isoprene chloroacetate is described in copending application Ser. No. 359,011, filed by Carlos G. Cardenas. The present invention has particular application in the preparation of an intermediate suitable for the method of said copending application.

What is claimed is:

1. In a process for addition halogenation of a conjugated diene with an elemental halogen of the group consisting of chlorine and bromine under halogenation conditions, the improvement for obtaining increased yield of 1,2- and 1,4-dihalogenated butene addition products comprising forming a reaction mixture comprising said conjugated diene and a dipolar aprotic solvent resistant to halogenation under such addition halogenation conditions in the proportion of about 0.1–0.6 moles dipolar aprotic solvent per mole of said diene.

2. The process of claim 1 wherein the molar ratio of chlorine to conjugated diene is less than 1:1.

3. The process of claim 1 wherein 1,4-dihalogenated butene and 1,2 halogenated butene products are recovered from said reaction mixture and the recovered 1,2-dihalogenated-3-butene product is converted into additional 1,4-dihalogenated butene product.

4. The process of claim 1 where the halogen is chlorine.

5. The process of claim 1 wherein the conjugated diene is isoprene.

6. The process of claim 1 wherein the aprotic solvent is dimethylformamide.

7. The process of claim 1 wherein the aprotic solvent is N,N-dimethylacetamide.

8. The process of claim 1 wherein the aprotic solvent is hexamethylphosphoramide.

9. The process of claim 1 wherein the reaction is carried out at about room temperature.

* * * * *

UNITED STATES PATENT AND TRADEMARK OFFICE
CERTIFICATE OF CORRECTION

PATENT NO. : 3,932,543

DATED : January 13, 1976

INVENTOR(S) : Richard A. Von Genk and Carlos G. Cardenas

It is certified that error appears in the above-identified patent and that said Letters Patent are hereby corrected as shown below:

Column 4, Table 4, in column under "1 hr. 25°", change "119" to --9--.

Signed and Sealed this thirteenth Day of April 1976

[SEAL]

Attest:

RUTH C. MASON
Attesting Officer

C. MARSHALL DANN
Commissioner of Patents and Trademarks